United States Patent
Adachi et al.

(10) Patent No.: US 11,617,841 B2
(45) Date of Patent: Apr. 4, 2023

(54) FINE WATER DISCHARGE DEVICE OF HUMAN BODY

(71) Applicant: AISIN CORPORATION, Aichi (JP)

(72) Inventors: Yoko Adachi, Kariya (JP); Shinsuke Inoue, Kariya (JP); Akiyoshi Hirano, Kariya (JP); Masayuki Miyabe, Kariya (JP)

(73) Assignee: AISIN CORPORATION, Kariya (JP)

( * ) Notice: Subject to any disclaimer, the term of this patent is extended or adjusted under 35 U.S.C. 154(b) by 120 days.

(21) Appl. No.: 16/818,785

(22) Filed: Mar. 13, 2020

(65) Prior Publication Data

US 2021/0030976 A1    Feb. 4, 2021

(30) Foreign Application Priority Data

Jul. 30, 2019  (JP) .............................. JP2019-139694

(51) Int. Cl.
*A61M 11/04*   (2006.01)
*A61H 33/12*   (2006.01)
(Continued)

(52) U.S. Cl.
CPC ........... *A61M 11/042* (2014.02); *A61H 33/12* (2013.01); *A61H 33/14* (2013.01); *A61N 1/44* (2013.01); *A61H 2205/022* (2013.01)

(58) Field of Classification Search
CPC ........ A61H 7/003; A61H 7/002; A61H 21/00; A61H 33/60; A61H 2201/1635;
(Continued)

(56) References Cited

U.S. PATENT DOCUMENTS

| 4,087,495 A | * | 5/1978 | Umehara | .................. F24F 6/12 |
| | | | | 261/81 |
| 4,952,283 A | * | 8/1990 | Besik | ..................... F24F 3/1411 |
| | | | | 165/4 |
| 2003/0150328 A1 | * | 8/2003 | Hansson | .............. A61G 13/108 |
| | | | | 95/273 |

(Continued)

FOREIGN PATENT DOCUMENTS

| JP | 2016-176658 A | 10/2016 |
| JP | 2017-060939 A | 3/2017 |

(Continued)

*Primary Examiner* — Timothy A Stanis
*Assistant Examiner* — Alexander Morales
(74) *Attorney, Agent, or Firm* — Oblon, McClelland, Maier & Neustadt, L.L.P.

(57) ABSTRACT

A fine water discharge device of a human body which discharges fine water to the human body includes: fine water generating units being brought into a moisture absorption state and a moisture release state in which moisture is absorbed in, and is released from, a conductive polymer film due to a decrease and an increase in temperature, respectively and disposed in parallel; a blowing unit blowing air so that air flows through the fine water generating units; an electrifying portion individually electrifying the fine water generating units so that a temperature of each fine water generating unit is changed depending on electrification; and a control portion controlling the electrifying portion and the blowing unit so that the fine water generating units are individually switched between the moisture absorption state and the moisture release state to discharge the fine water by blowing air.

18 Claims, 11 Drawing Sheets

(51) Int. Cl.
*A61H 33/14* (2006.01)
*A61N 1/44* (2006.01)

(58) Field of Classification Search
CPC .... A61H 2201/0115; A61H 2201/0107; A61H 2201/0153; A61H 2201/1685; A61H 2201/1215; A61H 2201/5015; A61H 2201/5035; A61H 2201/5064; A61H 2201/5066
USPC .................................................... 128/200.24
See application file for complete search history.

(56) References Cited

U.S. PATENT DOCUMENTS

| | | | | |
|---|---|---|---|---|
| 2006/0277873 | A1* | 12/2006 | Lyons | B01D 46/10 55/416 |
| 2008/0229606 | A1* | 9/2008 | Hirai | F24F 5/0035 34/97 |
| 2010/0061896 | A1* | 3/2010 | Sassoon | A61L 9/035 43/132.1 |
| 2011/0268605 | A1* | 11/2011 | Haran | B05B 17/0646 422/4 |
| 2014/0210114 | A1* | 7/2014 | Staniforth | F04F 5/24 261/30 |
| 2015/0107016 | A1* | 4/2015 | Mizuno | A45D 19/10 4/515 |
| 2015/0366323 | A1* | 12/2015 | Bouix | H05B 3/146 206/581 |
| 2016/0061475 | A1* | 3/2016 | Ito | F24F 3/1411 165/4 |
| 2016/0088931 | A1* | 3/2016 | Schneider | A47B 21/03 361/679.08 |

FOREIGN PATENT DOCUMENTS

| | | | |
|---|---|---|---|
| JP | 2017116130 A | * | 6/2017 |
| JP | 2018-054258 A | | 4/2018 |
| JP | 2019-018195 A | | 2/2019 |

* cited by examiner

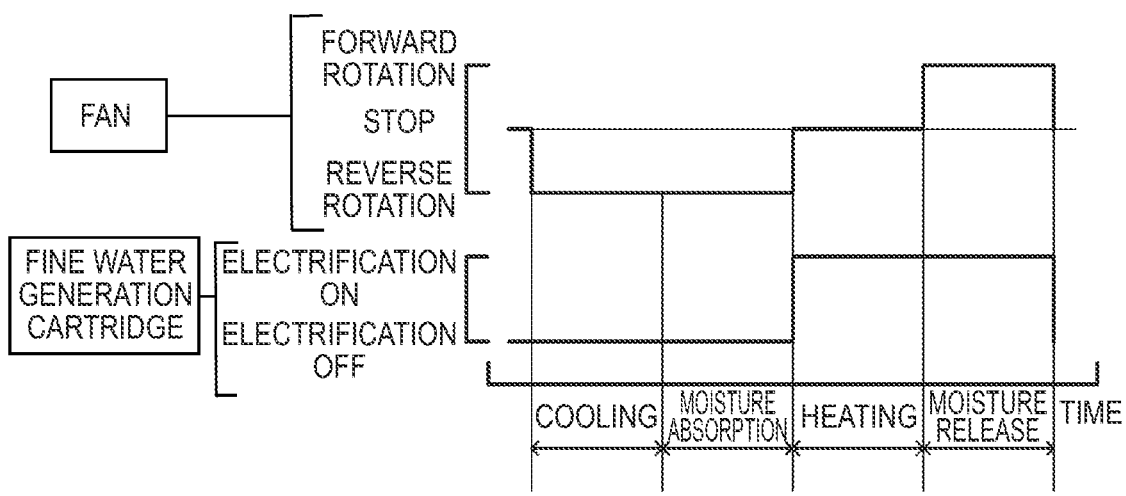
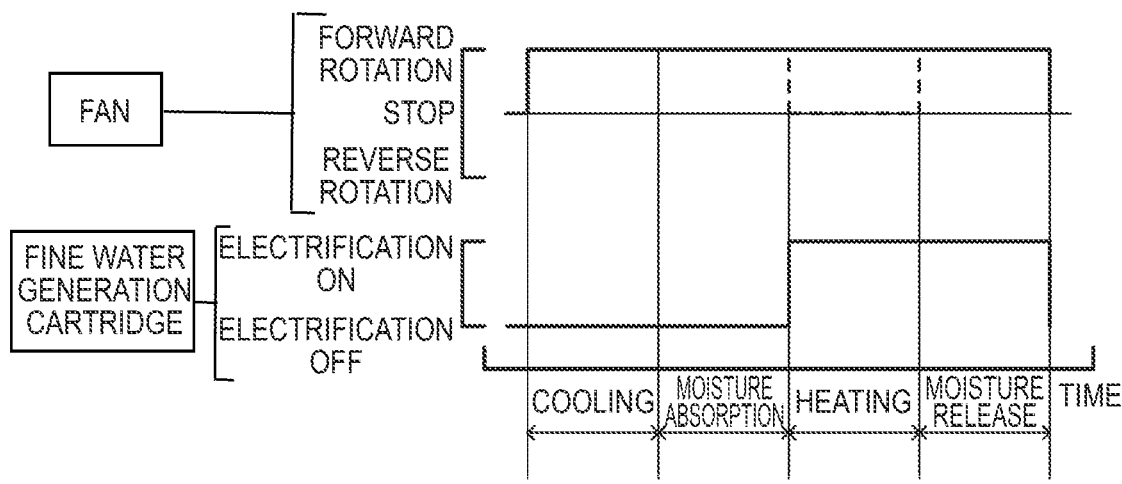

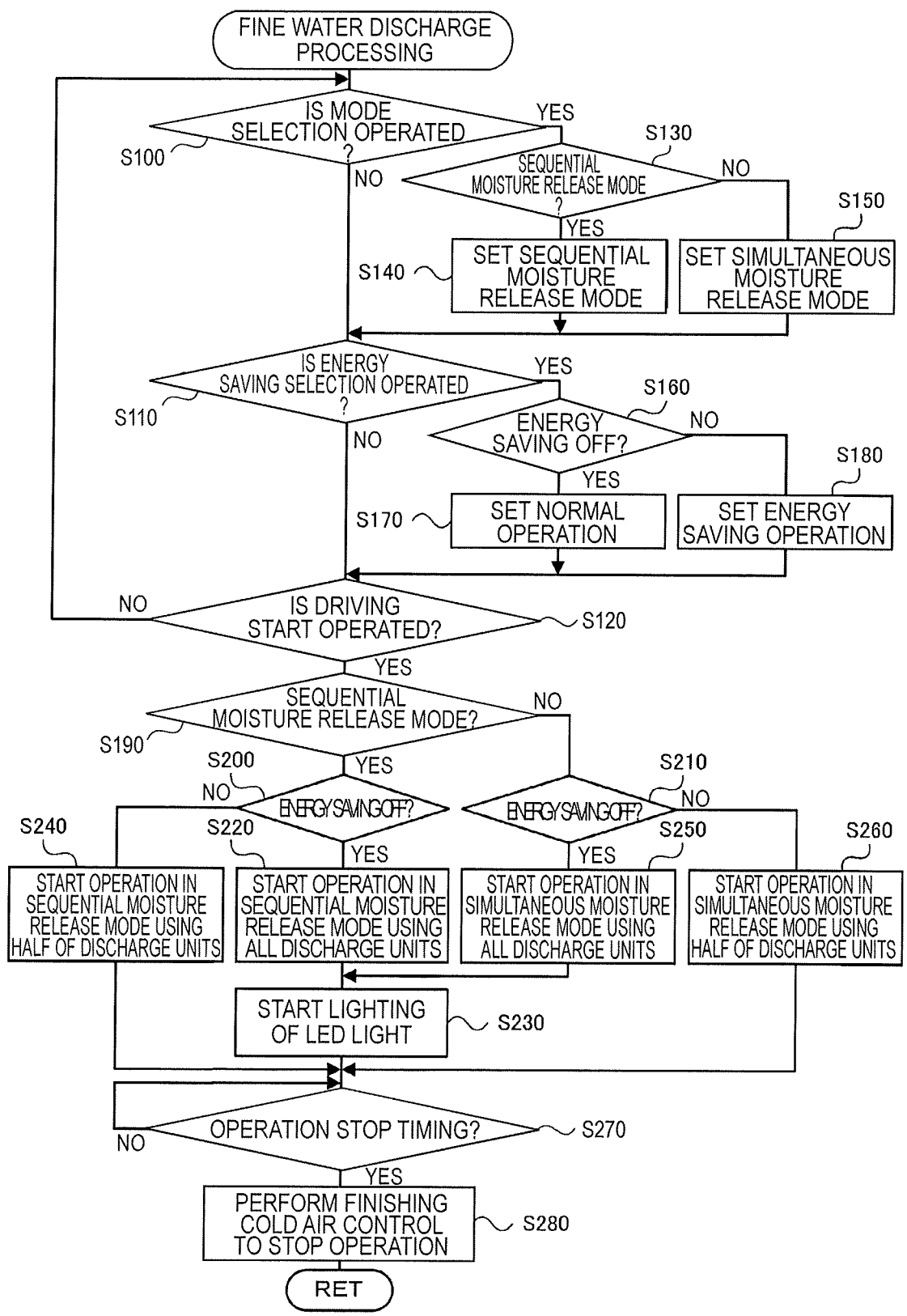

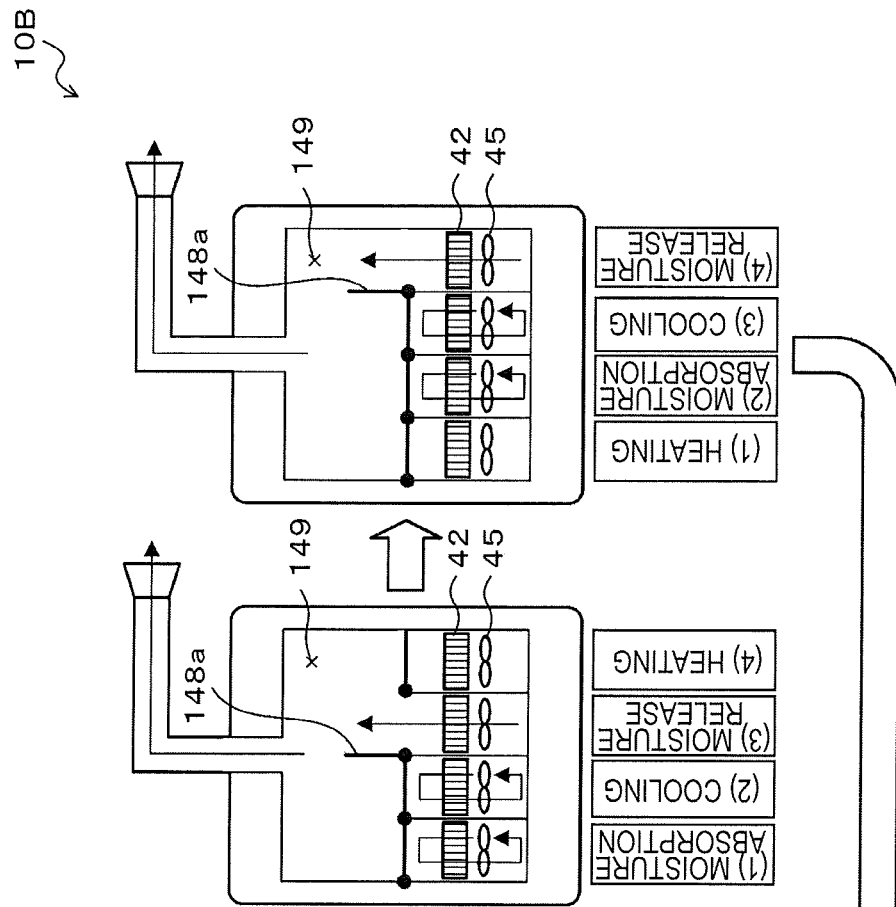

FINE WATER DISCHARGE DEVICE OF HUMAN BODY

CROSS REFERENCE TO RELATED APPLICATIONS

This application is based on and claims priority under 35 U.S.C. § 119 to Japanese Patent Application 2019-139694, filed on Jul. 30, 2019, the entire contents of which are incorporated herein by reference.

TECHNICAL FIELD

This disclosure relates to a fine water discharge device of a human body.

BACKGROUND DISCUSSION

In the related art, a device capable of discharging moisture toward a treatment target such as a human face is known. For example, JP 57-74041UM-A discloses a device which discharges steam generated by heating water stored in a tank by a heater to a treatment target via a steam introduction pipe. JP 2017-116130A discloses a device in which a plurality of moisture absorption/release units, which are changed to a moisture absorption state in which moisture in air is absorbed and a moisture release state in which the absorbed moisture is released to generate fine water, are disposed in series (single row) along a flow direction of the air. In this device, each moisture absorption/release unit is independently controlled to be in a moisture absorption state or a moisture release state to discharge the fine water to a treatment target.

Unlike the device of JP 57-74041UM-A, in the device of JP 2017-116130A described above, there is no need to supply water to the tank, and since high-temperature steam is not discharged, each portion is not necessary to have a heat-resistant structure. However, since the moisture absorption/release units are disposed in series, it is necessary to prevent the fine water released from the moisture absorption/release unit on an upstream side of the air from being absorbed by the moisture absorption/release unit on the downstream side. Therefore, after each moisture absorption/release unit is in the moisture absorption state, when the moisture is sequentially released from the moisture absorption/release unit on the upstream side to the moisture absorption/release unit on the downstream side, the moisture absorption/release unit which has completed the moisture release is controlled to be in the moisture absorption state again. However, after a moisture absorption/release unit on a most downstream side is finally brought into the moisture release state and completes the moisture release, the moisture absorption/release unit on the upstream side needs to wait the moisture release until the moisture absorption/release unit on the most downstream side is brought into the moisture absorption state and completes the moisture absorption. As described above, even if the plurality of moisture absorption/release units are provided, an operation may be restricted, and thus, there is still room for improvement.

Thus, a need exists for a fine water discharge device of human body which is not susceptible to the drawback mentioned above.

SUMMARY

This disclosure adopts the following means to achieve the above-described main object.

A fine water discharge device of human body according to an aspect of this disclosure discharges fine water to the human body, and the device includes: a plurality of fine water generating units which are brought into a moisture absorption state in which moisture in air is absorbed in a conductive polymer film due to a decrease in temperature and a moisture release state in which the absorbed moisture is released from the conductive polymer film as fine water due to an increase in temperature and are disposed in parallel; a blowing unit which blows air so that air flows through the fine water generating units; an electrifying portion which individually electrifies the plurality of fine water generating units so that a temperature of each fine water generating unit is changed depending on presence or absence of electrification; and a control portion which controls the electrifying portion and the blowing unit so that the plurality of fine water generating units are individually switched between the moisture absorption state and the moisture release state to discharge the fine water by blowing air.

BRIEF DESCRIPTION OF THE DRAWINGS

The foregoing and additional features and characteristics of this disclosure will become more apparent from the following detailed description considered with the reference to the accompanying drawings, wherein:

FIGS. 7A and 7B are explanatory diagrams illustrating an example of a control pattern of the fine water discharge unit;

FIG. 8 is a flowchart illustrating an example of fine water discharge processing;

FIG. 14 is an explanatory diagram illustrating a state in which the fine water discharge device is operated in the sequential moisture release mode.

DETAILED DESCRIPTION

Next, embodiments of the present disclosure will be described.

Figure 1:
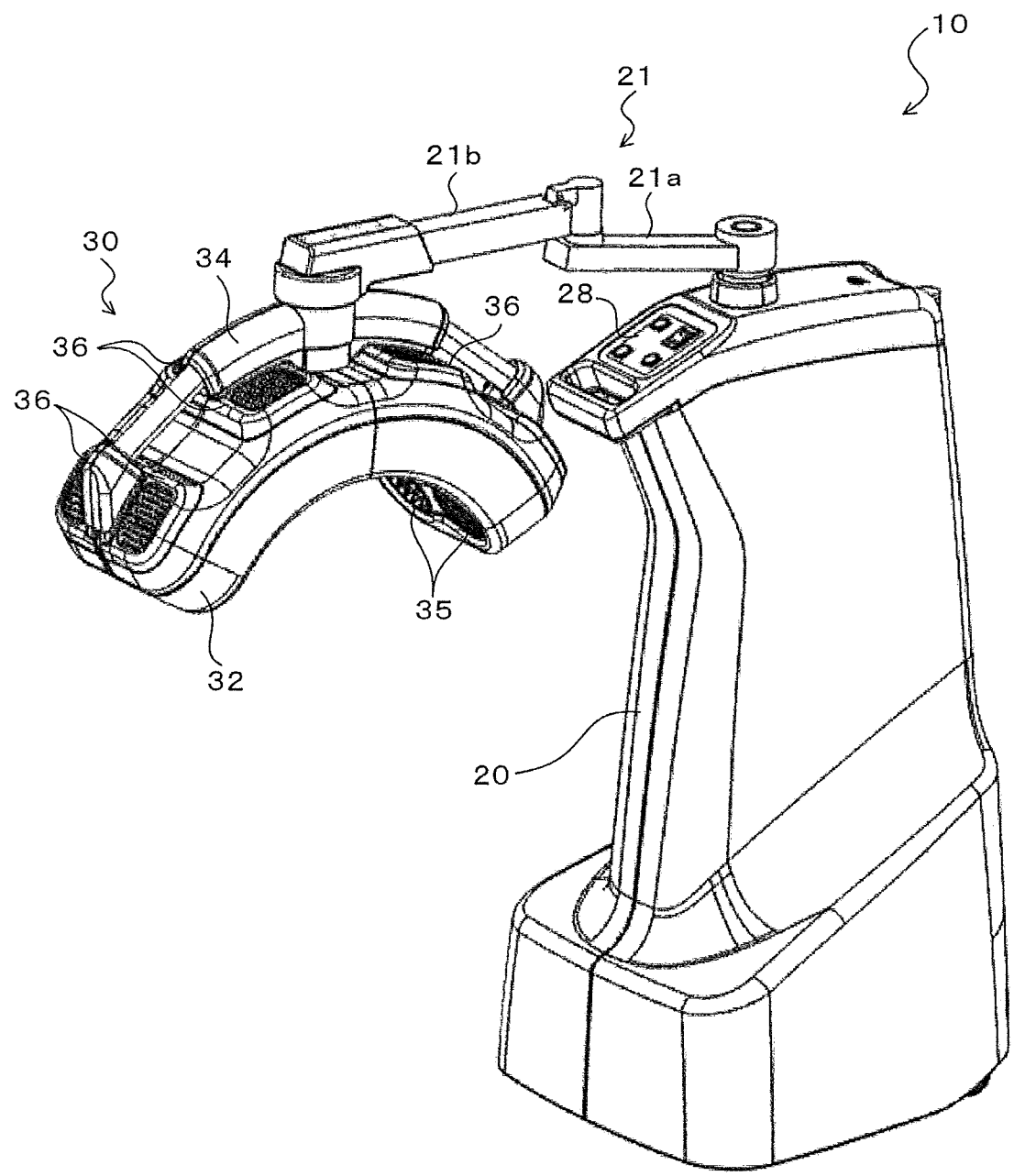
FIG. 1 is an external perspective view of a fine water discharge device.
Figure 2A:
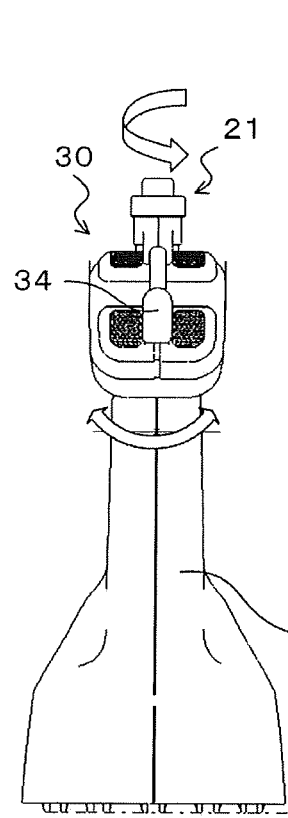
FIGS. 2A and 2B are a front view and a side view of the fine water discharge device.
Figure 2B:
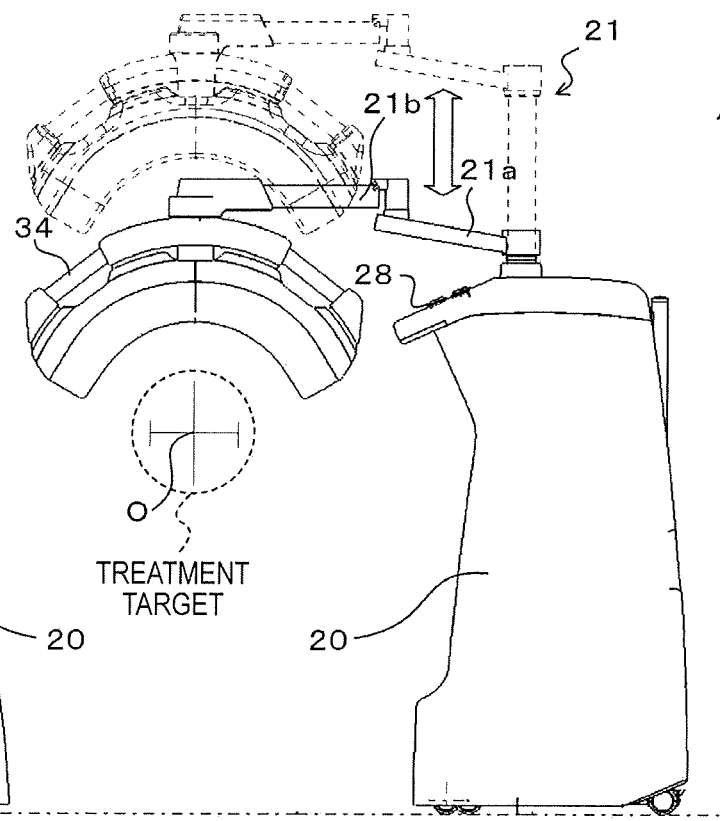
Figure 3:
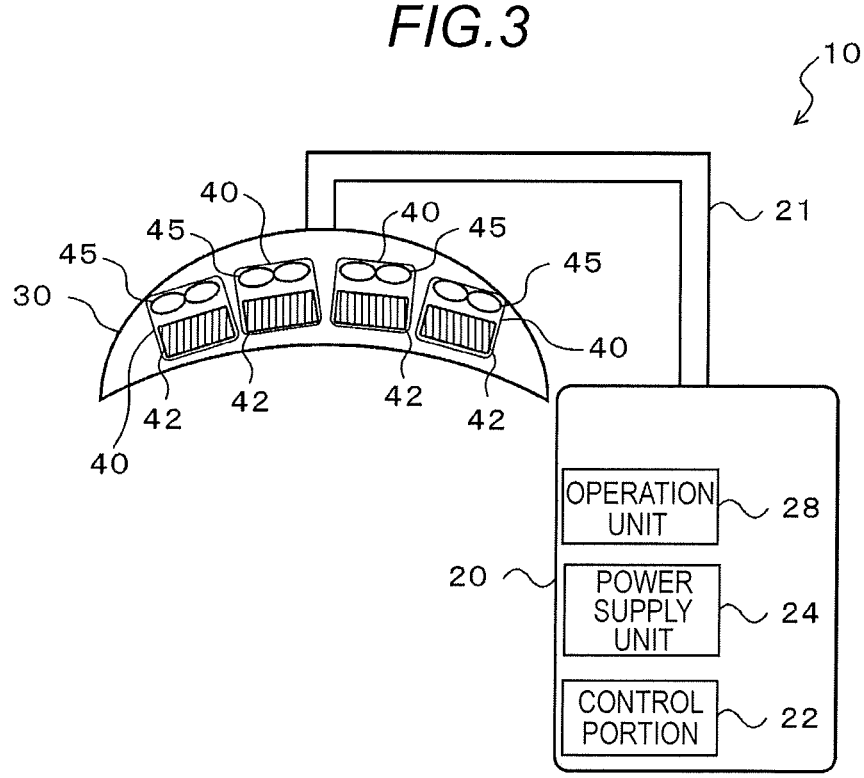
FIG. 3 is a configuration diagram schematically illustrating a configuration of the fine water discharge device.

FIG. 1 is an external perspective view of a fine water discharge device 10, FIGS. 2A and 2B are a front view and a side view of the fine water discharge device 10, and FIG. 3 is a configuration diagram schematically illustrating a configuration of the fine water discharge device 10. FIG. 2A is the front view and FIG. 2B is the side view. The fine water discharge device 10 of the present embodiment is used for a beauty purpose, a medical purpose, or the like which discharges fine water to a treatment target of a human body such as a facial skin and hair. As shown in FIGS. 1 to 3, this fine water discharge device 10 includes a device main body 20, a movable arm 21, and a discharge head 30. The movable arm 21 includes a first arm 21a which is attached to an upper portion of the device main body 20 so as to be vertically expandable and contractable and to be horizontally turnable, and a second arm 21b attached to a tip of the first arm 21a so as to be turnable horizontally. A holding arm 34 of the discharge head 30 is attached to a tip of the second arm 21b so as to be horizontally turnable. Accordingly, the discharge head 30 can move and turn in an up-down direction, a left-right direction, and a front-rear direction with respect to the device main body 20, and can be adjusted to a position suitable for a treatment target.

Figure 4A:
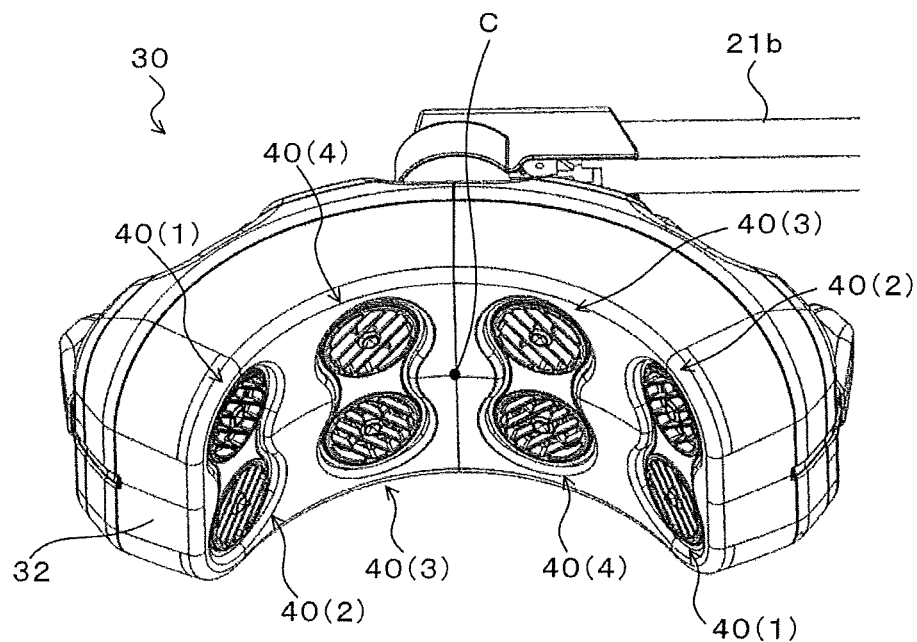
FIGS. 4A and 4B are perspective views of a discharge head.
Figure 4B:
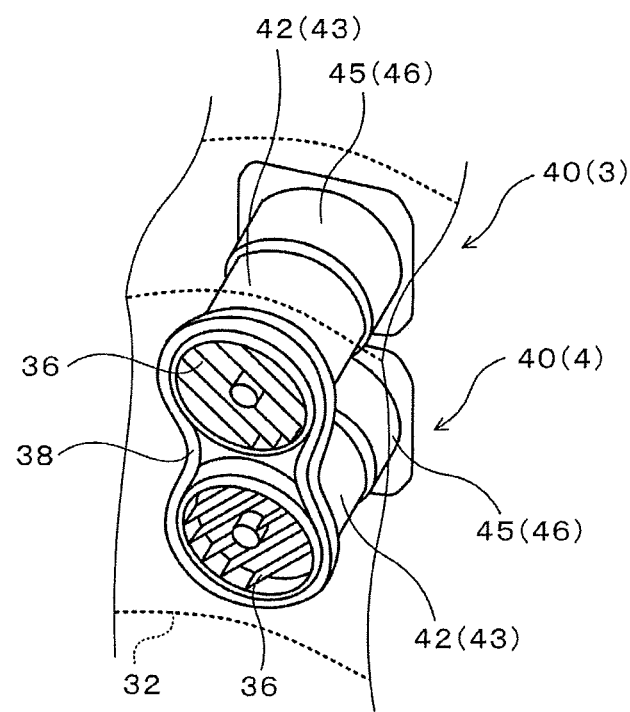
Figure 5:
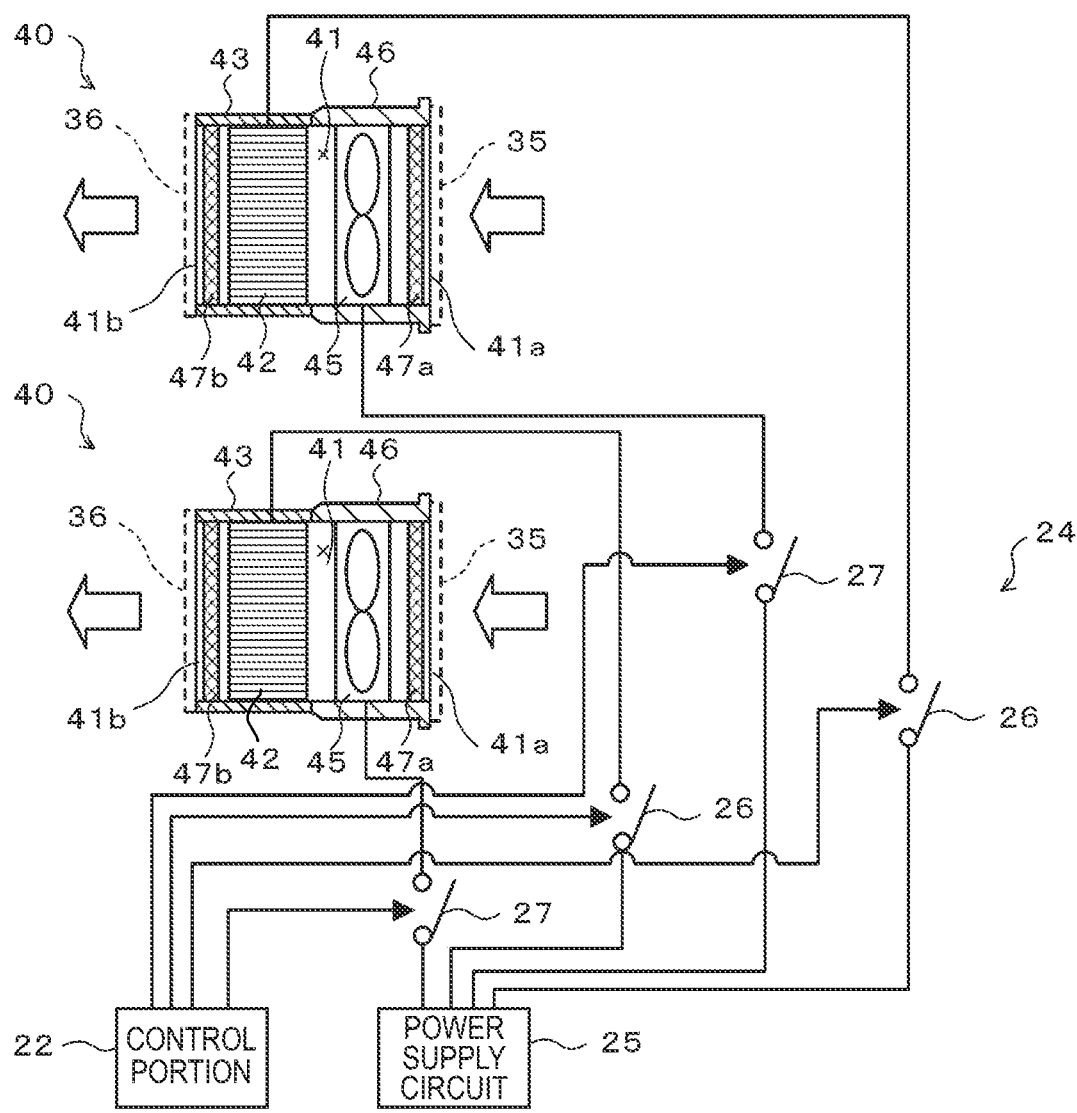
FIG. 5 is a configuration diagram schematically illustrating a configuration of a fine water discharge unit.
Figure 6A:
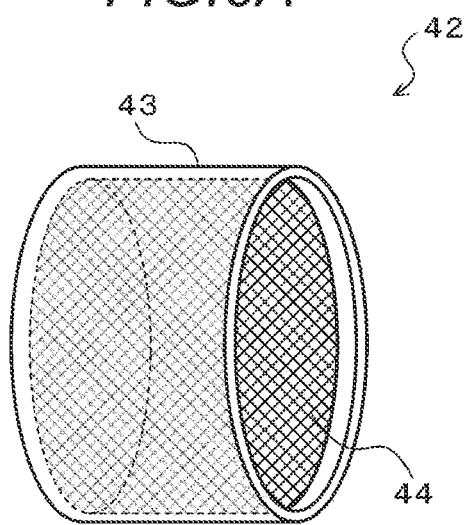
FIGS. 6A and 6B are configuration diagrams schematically illustrating a configuration of a fine water generation cartridge.
Figure 6B:
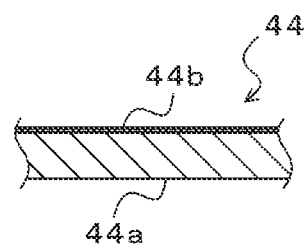

The discharge head 30 includes a head main body 32 which is curved in an arc shape in a side view, the holding arm 34 which holds the head main body 32, is attached to the second arm 21b, and is curved along an upper surface of the head main body 32, and a plurality of fine water discharge units 40 which are disposed in the head main body 32. FIGS. 4A and 4B are perspective views of the discharge head 30, FIG. 5 is a configuration diagram schematically illustrating a configuration of the fine water discharge unit 40, and FIGS. 6A and 6B are configuration diagrams schematically illustrating a configuration of a fine water generation cartridge 42. FIG. 4A is an overall perspective view illustrating an appearance of the discharge head 30, and FIG. 4B is a partially perspective view illustrating an inside of the discharge head 30. FIG. 6A is a perspective view illustrating the configuration of the fine water generation cartridge 42, and FIG. 6B is a cross-sectional view illustrating a configuration of a fine water generation element 44. As illustrated in FIG. 4A, the plurality (for example, eight) of fine water discharge units 40 are disposed in parallel in the head main body 32 of the discharge head 30. The eight fine water discharge units 40 are disposed in four sets of two adjacent units, and two fine water discharge units in each of pairs are disposed at two positions which are point-symmetric with respect to a center C (turning center) of the discharge head 30. Pairs of two fine water discharge units 40 are referred to as fine water discharge units 40(1), 40(2), 40(3), and 40(4), respectively. As illustrated in FIG. 5, each fine water discharge unit 40 includes one fine water generation cartridge 42, one fan 45, and filters 47a and 47b.

In the fine water generation cartridge 42, the fine water generation element 44 is accommodated in a substantially cylindrical case 43, the filter 47a is attached to one end of the case 43, and the filter 47b is attached to the other end thereof. The fan 45 is a propeller fan which is rotatably driven by a motor (not illustrated) and is accommodated in a substantially cylindrical case 46. The fan 45 may be a sirocco fan or the like. The case 43 of the fine water generation cartridge 42 and the case 46 of the fan 45 are formed to have substantially the same inner diameter and form one cylindrical flow path 41 in the discharge head 30. The fan 45 sucks air into the flow path 41 from a suction port 41a at one end of the case 46 via a filter cover 35 by a forward rotation of the motor. The air sucked into the flow path 41 flows through the filter 47a, the fine water generation element 44 of the fine water generation cartridge 42, and the filter 47b, and is blown from the discharge port 41b at one end of the case 43 to an outside via a filter cover 36. Each fine water discharge unit 40 is disposed so that an axis center thereof is orthogonal to an arc of the head main body 32. Accordingly, each of the plurality of fans 45 blows air from the flow path 41 toward an arc center O (refer to FIGS. 2A and 2B). As illustrated in FIG. 4B, the head main body 32 includes a single oval LED light 38 of which a center is narrowed around the filter covers 36 of one set of adjacent two fine water discharge units 40. Accordingly, in a case where a position of the head main body 32 is adjusted so that the head main body 32 faces a face of a treatment target person, the treatment target person can visually recognize light of the LED light 38.

As illustrated in FIGS. 6A and 6B, the fine water generation element 44 of the fine water generation cartridge 42 includes a base material 44a and a conductive polymer film 44b formed on a surface of the base material 44a. The base material 44a is formed of a conductive material such as a metal material such as a stainless metal or a copper metal, a carbon material, or a conductive ceramic material. In the present embodiment, a stainless steel metal foil to which aluminum is added is used. The fine water generation element 44 may be constituted by a plurality of the flat base materials 44a so that air can flow therethrough and a surface area of the base material 44a (conductive polymer film 44b) is as large as possible, or may be constituted by a base material 44a formed in a honeycomb shape or a spiral shape.

The conductive polymer film 44b is formed of a conductive polymer compound such as a thiophene-based conductive polymer. In the present embodiment, the conductive polymer film 44b is formed of PEDOT/PSS (poly (3,4-ethylenedioxythiophene)/poly (styrenesulfonic acid)) out of the thiophene-based conductive polymers. PEDOT/PSS is a core-shell structure having a core of PEDOT and a shell of a sulfonic acid group which is an acidic functional group capable of hydrogen bonding. In the conductive polymer film 44b, a laminated structure in which PEDOT/PSS shells are arranged is formed, and for example, a nanochannel, which is a nanometer-sized flow path such as 2 nanometers, is formed between the shells. A large amount of sulfonic acid groups exist in the nanochannel. Accordingly, in a case where a moisture content on the surface of the conductive polymer film 44b is large and a moisture content therein is small, the moisture existing on the surface of the conductive polymer film 44b moves inside the conductive polymer film 44b through the sulfonic acid groups in the nanochannel due to a concentration difference between the surface and the inside. Accordingly, the conductive polymer film 44b absorbs (adsorbs) the moisture. In a case where the moisture content on the surface is small and the moisture content inside is large in a state where the moisture is absorbed to the inside, the moisture moves to the surface through the sulfonic acid groups in the nanochannel due to the concentration difference between the surface and the inside. Therefore, the moisture is released from the conductive polymer film 44b as the fine water. If a temperature of the conductive polymer film 44b is increased by electrification from a power supply unit 24 described later, quick release of the moisture (fine water) is promoted as compared with a case where the moisture is moved only by the concentration difference. Moreover, if the temperature of the conductive polymer film 44b is reduced by the air blown from the fan 45 in a state in which the electrification from the power supply unit 24 is stopped, quick absorption of the moisture is promoted as compared with the case where the moisture is moved only by the concentration difference. As described above, the fine water generation cartridge 42 (the fine water generation element 44) is changed into a moisture absorption state in which the moisture in the air is absorbed by the conductive polymer film 44b due to the decrease in the temperature and a moisture release state in which the absorbed moisture is released from the conductive polymer film 44b by the increase in the temperature. A thickness of the conductive polymer film 44b can be appropriately determined according to a required moisture absorption amount (moisture release amount) of the fine water. For example, in a case where the conductive polymer film 44b is formed so as to have a thickness of 1 to 30 micrometers or the like, it is possible to absorb sufficient moisture to discharge the fine water for about ten seconds to several tens of seconds.

The fine water generation cartridge 42 generates uncharged fine water having a water particle size of 50 nanometers or less, for example, 2 nanometers or less, from the conductive polymer film 44b of the fine water generation element 44. It is considered that the reason why the fine water has the particle size because a size of the nanochannel is 2 nanometers or less, and thus, mobility of the water in the nanochannel is improved or a pressure increases due to the increase in the temperature of the conductive polymer film, and the moisture jumps out of the nanochannel. Even if the water particles aggregate after the water jumps out, the particle size is distributed in a range of 50 nanometers or less. The generation of the fine water in the fine water generation cartridge 42 (conductive polymer film 44b) is described in detail in the specification of Japanese Patent Application No. 2018-172166 of the applicant of the present disclosure, and thus, more detailed descriptions are omitted.

The device main body 20 includes a control portion 22, the power supply unit 24, and an operation unit 28. The operation unit 28 is provided on an upper surface of the device main body 20 and includes a plurality of operation switches or operation buttons for turning on/off power, selecting an operation mode, selecting energy saving, or the like. The power supply unit 24 includes a power supply circuit 25 to which electric power such as AC 100 V is supplied and which converts the electric power into electric power suitable for driving each unit such as the motor of the fan 45, the fine water generation cartridge 42 (fine water generation element 44), or the LED light 38 as necessary and outputs the converted electric power, and change-over switches 26 and 27 for switching whether or not to electrify each unit. An operation signal from the operation unit 28 is input to the control portion 22. The control portion 22 controls the change-over switch 26 which switches whether or not to electrify the fine water generation cartridge 42 (the fine water generation element 44) of each fine water discharge unit 40, or controls the change-over switch 27 which switches whether or not to operate the fan 45 of each fine water discharge unit 40. In FIG. 5, illustration of a configuration for switching whether or not to electrify the LED light 38 is omitted.

Here, FIGS. 7A and 7B are explanatory diagrams illustrating an example of a control pattern of the fine water discharge unit 40. FIG. 7A illustrates a pattern of a bidirectional rotation control for rotating the fan 45 in a forward direction and a reverse direction, and FIG. 7B illustrates a pattern of a unidirectional rotation control for rotating the fan 45 in the forward direction without rotating the fan 45 in the reverse direction. In the bidirectional rotation control of FIG. 7A, the electrification to the fine water generation cartridge 42 (the fine water generation element 44) is stopped and the fan 45 is rotated in the reverse direction, and thus, the fine water generation element 44 is cooled. Accordingly, moisture is absorbed by the conductive polymer film 44b which has a relatively low temperature due to the cooling. Next, the fan 45 is stopped and the fine water generation cartridge 42 is electrified to heat the fine water generation element 44 so as to increase the temperature of the fine water generation element 44. Then, the fine water generation cartridge 42 is electrified to rotate the fan 45 in the forward direction such that the fine water is released from the conductive polymer film 44b which has a relatively high temperature and is discharged to the outside by blowing air. In this way, the cooling, the moisture absorption, the heating, and the moisture release are defined as one cycle, and each fine water discharge unit 40 is controlled by repeating this cycle. In the bidirectional rotation control, air is blown toward the treatment target at the time of the moisture release. However, the air is not blown toward the treatment target at the time of the cooling, the moisture absorption, or the heating. According to a temperature state of the fine water generation element 44, the moisture absorption is performed during the cooling, and the moisture release is performed during the heating. Meanwhile, in the unidirectional rotation control of FIG. 7B, the electrification to the fine water generation cartridge 42 is stopped and the fan 45 is rotated in the forward direction such that the cooling and the moisture absorption are performed. The fan 45 is rotated in the forward direction not only at the time of the moisture release but also at the time of the heating. Therefore, the cooling and the moisture absorption have the same operation content as each other, and the heating and the moisture release also have the same operation content as each other. As described above, in the unidirectional rotation control, air is blown toward the treatment target not only at the time of the moisture release but also at the time of the cooling, the moisture absorption, or the heating. At the time of the heating, as in the case of the bidirectional rotation control, the fan 45 may be stopped (refer to dotted lines) so that air is not blown.

Next, an operation of the fine water discharge device 10 configured as described above will be described. FIG. 8 is a flowchart illustrating an example of fine water discharge processing. The fine water discharge processing is performed in a case where power of the fine water discharge device 10 is turned on. In the fine water discharge processing, first, the control portion 22 determines whether or not a mode selection operation is performed by a practitioner or a user operating the operation unit 28 (S100), determines whether or not an energy saving selection operation is performed (S110), and determine whether or not a driving start operation is performed (S120).

If it is determined that the mode selection operation is performed in S100, it is determined whether or not a sequential moisture release mode is selected (S130). If it is determined that the sequential moisture release mode is selected, the sequential moisture release mode is set, and if it is determined that a simultaneous moisture release mode is selected instead of the sequential moisture release mode (S140), the simultaneous moisture release mode is set (S150). The sequential moisture release mode is a mode in which the pairs of two fine water discharge units 40(1) to 40(4) are set to the moisture release state in that order (predetermined order) to discharge the fine water, and the simultaneous moisture release mode is a mode in which all the fine water discharge units 40 to be used are simultaneously set to the moisture release state to discharge the fine water. The mode is set to the sequential moisture release mode in default. If it is determined that the energy saving selection operation is performed in S110, it is determined whether or not energy saving off is selected (S160). If it is determined that the energy saving off is selected, a normal operation is set (S170), and if it is determined that energy saving on instead of the energy saving off is selected, an energy saving operation is set (S180). In the normal operation, the operation is performed using all the fine water discharge units 40 (total of eight) in order to supply sufficient fine water. In the energy saving operation, a half (total of four) of the eight fine water discharge units 40 is operated by stopping one of each pair of the pairs of two fine water discharge units 40(1) to 40(4) and using the other thereof in order to supply necessary fine water while suppressing power consumption. The mode is set to the normal operation (energy saving off) in default.

If it is determined that the driving start operation is performed in S120, it is determined whether or not the operation mode is set to the sequential moisture release mode (S190) and whether or not the operation mode is set to the energy saving off (S200, S210). When it is determined that the normal operation (energy saving off) in the sequential moisture release mode is performed, the operation starts in the sequential moisture release mode using all the fine water discharge units 40 (S220), and lighting of the LED light 38 starts (S230). If it is determined that the energy saving operation (energy saving on) in the sequential moisture release mode is performed, the operation starts in the sequential moisture release mode using the half of the fine water discharge units 40 (S240). Meanwhile, if it is determined that the normal operation in the simultaneous moisture release mode is performed, the operation starts in the simultaneous moisture release mode using all the fine water discharge units 40 (S250), and the lighting of the LED light 38 starts (S230). If it is determined that the energy saving operation in the simultaneous moisture release mode is performed, the operation starts in the simultaneous moisture release mode using the half of the fine water discharge units 40 (S260). In S230, for example, the LED light 38 is turned on when the fine water discharge unit 40 corresponding to disposition of the LED light 38 is in the moisture release state and is turned off in other cases, or the LED light 38 is turned on in a first lighting color when the corresponding the fine water discharge unit 40 is in the moisture release state and is turned on in a second lighting color in other cases. Alternatively, regardless of the operation state of the fine water discharge unit 40, the LED light 38 may be turned on in a predetermined lighting mode, or the LED light 38 may be turned on in a different lighting mode for each mode. The lighting effect of the LED light 38 enhances stage effects during the treatment, and provides effects such as relaxing the practitioner. In the energy saving operation, the LED light 38 is not turned on during the operation. However, the present disclosure is not limited to this, and the LED light 38 may be turned on during the operation.

If the operation starts in this way, it waits for an operation stop timing (S270). In S270, in a case where the practitioner or the user operates the operation unit 28 to instruct stop of the operation or in a case where a time reaches an operation time set by a timer (not illustrated), it is determined that the timing is the operation stop timing. If the timing reaches the operation stop timing, the fan 45 is rotated in the forward direction in a state where the electrification to the fine water generation element 44 of each fine water discharge unit 40 used for the operation is stopped. Accordingly, after performing a finishing cold air control for simultaneously blowing the cold air from each fine water discharge unit 40 used for the operation, the operation is stopped (S280), and the fine water discharge processing ends.

Figure 9:
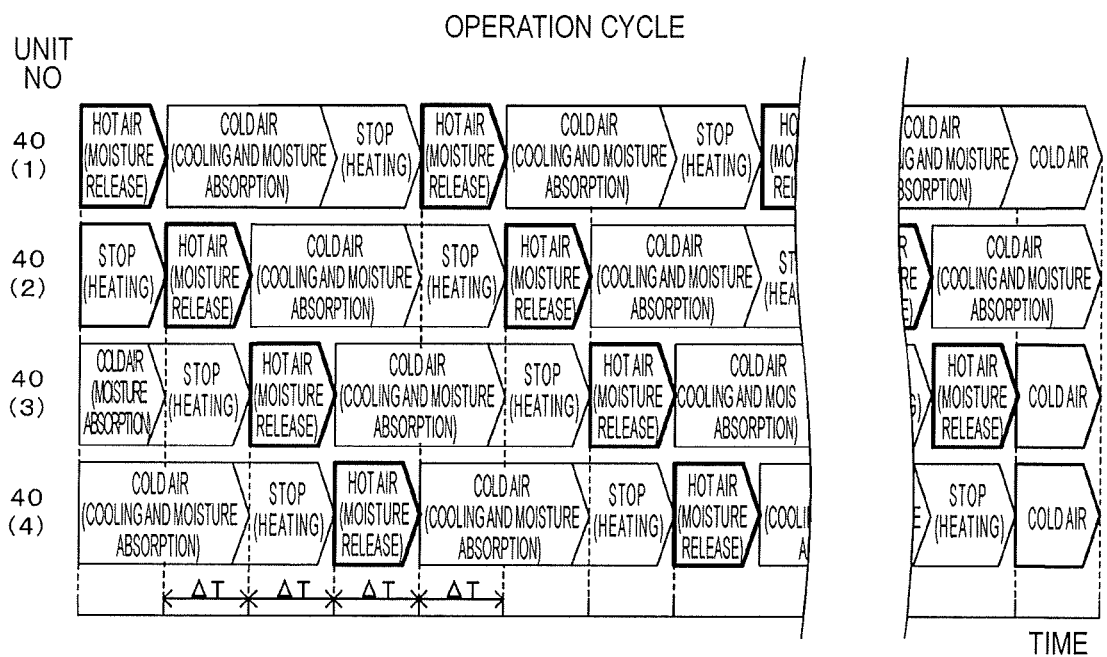
FIG. 9 is an explanatory diagram illustrating an example of an operation cycle in a sequential moisture release mode.
Figure 10:
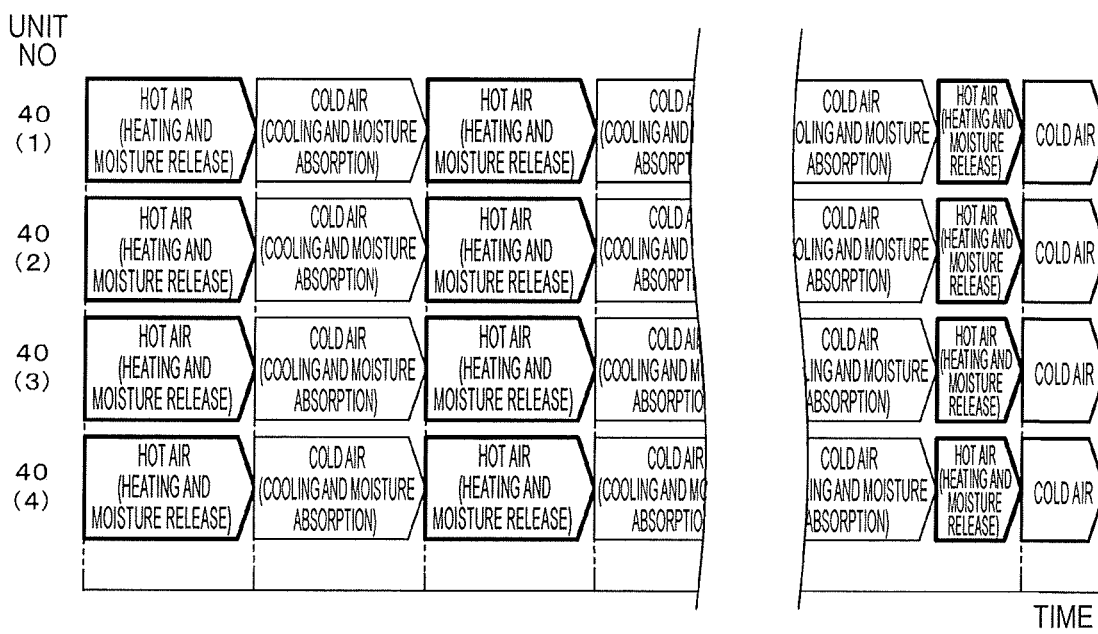
FIG. 10 is an explanatory diagram illustrating an example of an operation cycle in a simultaneous moisture release mode.
Figure 11A:
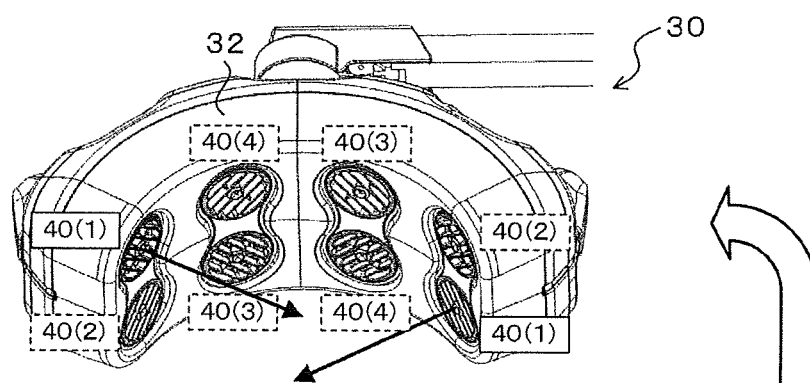
FIG. 11 is an explanatory diagram illustrating an operation state in the sequential moisture release mode.
Figure 11B:
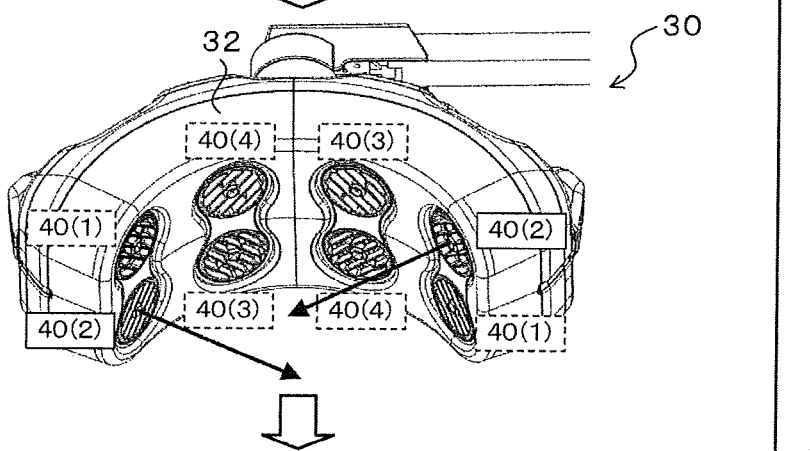
Figure 11C:
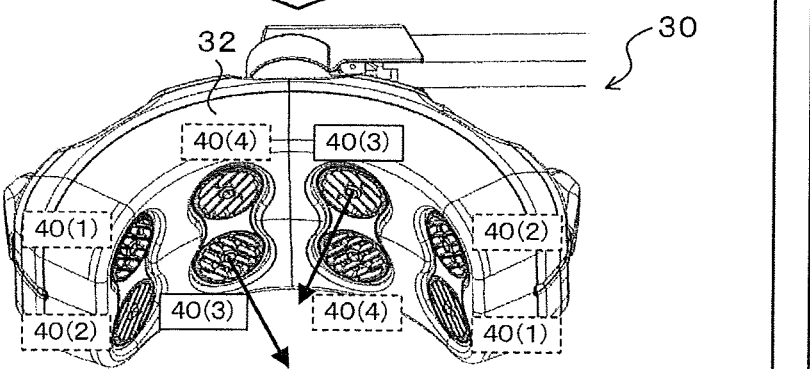
Figure 11D:
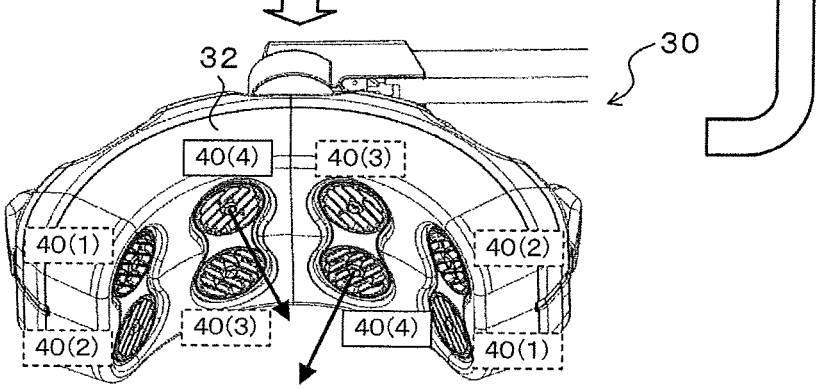

Here, FIG. 9 is an explanatory diagram illustrating an example of an operation cycle in the sequential moisture release mode, FIG. 10 is an explanatory diagram illustrating an example of an operation cycle in the simultaneous moisture release mode, and FIG. 11 is an explanatory diagram illustrating an operation state in the sequential moisture release mode. Unit Nos. (1) to (4) in FIGS. 9 and 10 illustrate the pairs of two fine water discharge units 40(1) to 40(4). In the sequential moisture release mode, as illustrated in FIG. 9, each unit of the fine water discharge units 40(1) to 40(4) is controlled by the bidirectional rotation control while being shifted by a time $\Delta T$ without synchronizing the cycles of the fine water discharge units 40(1) to 40(4). The time $\Delta T$ is set so that any one of the fine water discharge units 40(1) to 40(4) always releases moisture so as not to interrupt the discharge of the fine water. Therefore, in the discharge head 30, the fine water is continuously discharged by blowing hot air in order of the fine water discharge unit 40(1) (FIG. 11(a)), the fine water discharge unit 40(2) (FIG. 11(b)), the fine water discharge unit 40(3) (FIG. 11(c)), and the fine water discharge unit 40(4) (FIG. 11(d)). In the sequential moisture release mode, the control may be performed by the unidirectional rotation control, and the cold air may be blown toward the treatment target at the time of the cooling and at the time of the moisture absorption.

Meanwhile, in the simultaneous moisture release mode of FIG. 10, the cycles of the fine water discharge units 40(1) to 40(4) are synchronized, and each unit is controlled by the unidirectional rotation control. That is, in the simultaneous moisture release mode, the plurality of fine water generation cartridges 42 always blow air toward the treatment target while being individually switched between the moisture absorption (cooling/moisture absorption) and the moisture release (heating/moisture release). Accordingly, the hot air at the time of the heating/moisture release and the cold air at the time of the cooling/moisture absorption are alternately blown to the treatment target. In both modes, in the normal operation, each of the pairs of two fine water discharge units 40(1) to 40(4) is switched to the cooling, the moisture absorption, the heating, and the moisture release at the same timing. In both modes, the finishing cold air control is performed before the operation is stopped. The plurality of moisture release modes are switched in this manner, and thus, it is possible to perform an operation suitable for the treatment target or a treatment purpose or an operation suitable for a practitioner's preference.

In the fine water discharge device 10 of the present embodiment described above, the plurality of fine water generation cartridges 42 are disposed in parallel, and each fine water generation cartridge 42 can be individually switched between the moisture absorption (cooling/moisture absorption) and the moisture release (heating/moisture release). Accordingly, each fine water generation cartridge 42 can be switched to the moisture release at any timing to discharge the fine water, and restriction in the operation can be suppressed to increase a degree of freedom. Therefore, the operation suitable for the treatment target can be performed.

In the sequential moisture release mode, the fine water generation cartridges 42 are sequentially brought into the moisture release state. Accordingly, the discharge of the fine water is prevented from being interrupted, and the fine water can be stably supplied to the treatment target. Meanwhile, in the simultaneous moisture release mode, the fine water generation cartridges 42 are simultaneously brought into the moisture release state. Accordingly, a state where a large amount of fine water exists around the treatment target can be generated, and thus, the fine water can be sufficiently supplied to the treatment target. In the simultaneous moisture release mode, the hot air and the cold air are alternately blown. Accordingly, compared to a case where only the hot air is blown, it is possible to suppress the increase in the temperature around the treatment target and a comfortable treatment space can be provided. One moisture release mode out of the plurality of moisture release modes is selected and the operation is performed. Accordingly, the operation can be performed more appropriately according to the treatment target or the like. As described above, even in the sequential moisture release mode, the air may be always blown toward the treatment target so that the hot air and the cold air are alternately blown.

The fine water generation cartridges 42 are disposed in parallel in the discharge head 30 at the tip of the movable arm 21. Accordingly, the treatment target and the fine water generation cartridges 42 are close to each other, and thus, the fine water can be effectively supplied to the treatment target. The plurality of pairs of the fine water generation cartridges 42 are disposed symmetrically with respect to the center C of the discharge head 30, and each pair of the fine water generation cartridges 42 is switched between the moisture absorption and the moisture release at the same timing. Therefore, each pair of the fine water generation cartridges 42 discharges the fine water at the same timing. Accordingly, it is possible to uniformly disperse the fine water around the treatment target (treatment space) and supply fine water evenly to the treatment target.

The finishing cold air control is performed before the operation is stopped. Accordingly, an effect of tightening the skin of the treatment target can be exhibited, and the end of the operation (end of the treatment) can be notified. The conductive polymer film 44b is kept at a low temperature to promote the moisture absorption. Accordingly, preparation for the next treatment can be performed.

One fine water generation cartridge 42 and one fan 45 are provided as a set and the plurality of sets of the fine water discharge units 40 are disposed in parallel. Accordingly, it is possible to easily realize a configuration in which air can be individually blown to each fine water generation cartridge 42.

In the embodiment, the plurality of pairs of the fine water discharge units 40 (fine water generation cartridges 42) are disposed symmetrically with respect to the center C of the discharge head 30, and each pair of the fine water generation cartridges 42 is switched between the moisture absorption and the moisture release at the same timing. However, the present disclosure is not limited to this. For example, each pair of the fine water generation cartridges 42 may be switched between the moisture absorption and the moisture release at timings different from each other, or one set of the two fine water generation cartridges 42 may be switched between the moisture absorption and the moisture release at the same timing. As long as the plurality of fine water discharge units 40 is disposed in parallel in the discharge head 30, the fine water discharge units 40 may not be symmetrically disposed, and the fine water discharge unit 40 may be biased toward any area of the discharge head 30 depending on the treatment target or the treatment purpose.

In the embodiment, the finishing cold air control is performed before the operation is stopped. However, the present disclosure is not limited to this, and the finishing cold air control may not be performed.

In the embodiment, an example is described in which any one of the two moisture release modes such as the sequential moisture release mode and the simultaneous moisture release mode is selected. However, the present disclosure is not limited to this, and any one of a plurality of moisture release modes including the sequential moisture release mode (predetermined moisture release mode) may be selected. Alternatively, the present disclosure is not limited to a case where the moisture release mode can be selected, and the operation may be performed in one predetermined moisture release mode, for example, the sequential moisture release mode.

In the embodiment, in the case of the energy saving operation, one of each of the pairs of two fine water discharge units 40(1) to 40(4) is stopped and the operation is performed using the other. However, the disclosure is not limited to this, and any operation may be performed as long as the operation is performed with a smaller number of the fine water discharge units 40 used for the operation than in the normal operation. For example, in the case of the energy saving operation, only the fine water discharge units 40(1) and 40(2) out of the fine water discharge units 40(1) to 40(4) may be used, or four fine water discharge units 40 located at a right half or a left half of the discharge heads 30 may be used.

Figure 12:
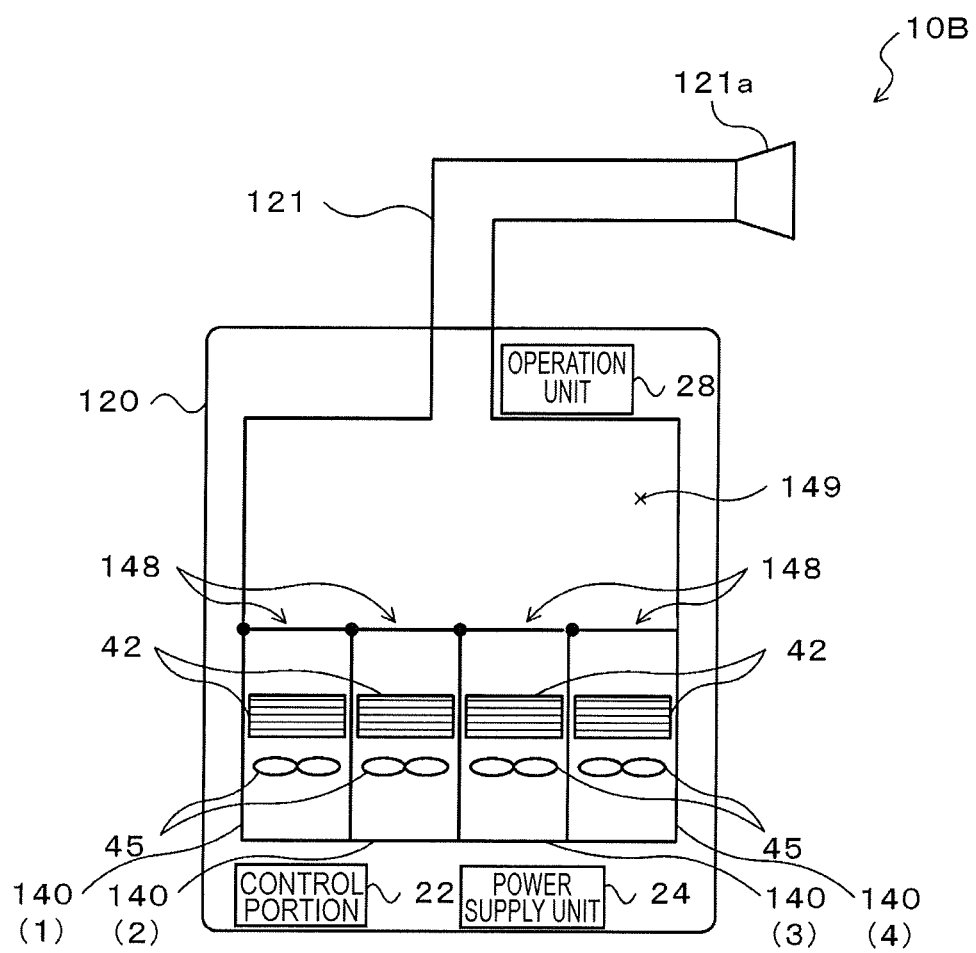
FIG. 12 is a configuration diagram schematically illustrating a configuration of a fine water discharge device of a modification example.
Figure 13:
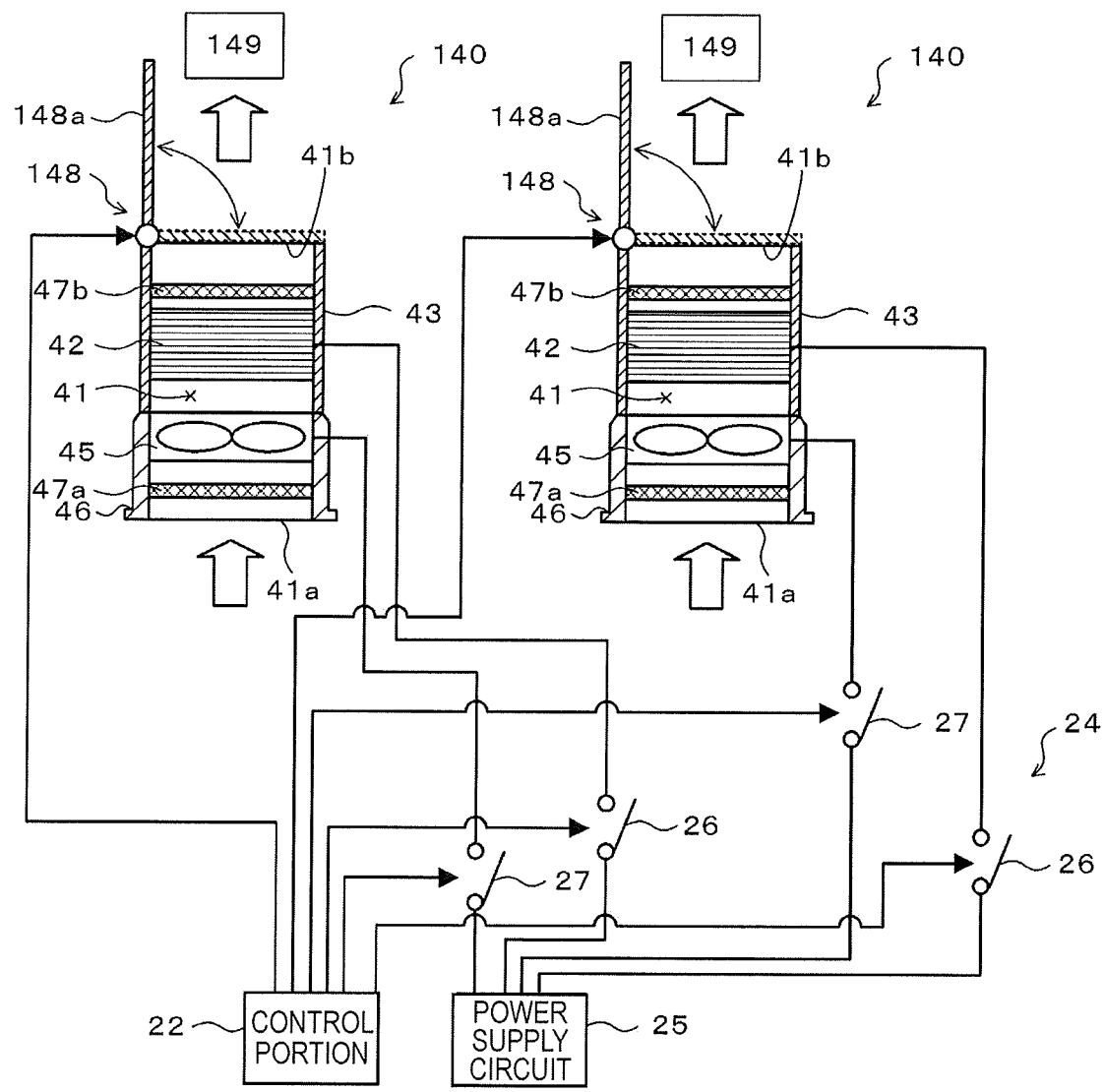
FIG. 13 is a configuration diagram schematically illustrating a configuration of a fine water discharge unit according to the modification example.

In the embodiment, the plurality of fine water discharge units 40 are disposed in the discharge head 30 attached to the tip of the movable arm 21. However, the present disclosure is not limited to this, and the plurality of fine water discharge units 40 may be disposed in a discharge head fixed to the device main body 20 or the like. Alternatively, the plurality of fine water discharge units 40 may be disposed in the device main body 20. FIG. 12 is a configuration diagram schematically illustrating a configuration of a fine water discharge device 10B of a modification example and FIG. 13 is a configuration diagram schematically illustrating a configuration of a fine water discharge unit 140 according to the modification example. In the modification example, the same reference numerals are assigned to the same configurations as those of the embodiment, and detailed descriptions thereof are omitted. As illustrated in FIG. 12, the fine water discharge device 10B of the modification example includes a plurality (for example, four) of fine water discharge units 140 and an air duct 121 through which air is blown toward a treatment target. A fine water storage chamber (fine water storage portion) 149 is formed in a device main body 120. Four fine water discharge units 140 are disposed adjacent to each other for convenience of illustration, but may be disposed to be arranged at equal intervals on the same circumference when viewed from above, for example.

Similarly to the fine water discharge unit 40 of the embodiment, each fine water discharge unit 140 includes the fan 45, the fine water generation cartridge 42, and the filters 47a and 47b, and air is sucked from the suction port 41a in the flow path 41 and discharged from the discharge port 41b. Each of the fine water discharge units 140 has the discharge port 41b communicating with the fine water storage chamber 149, and includes an opening/closing switching unit 148 capable of switching the opening and closing of the discharge port 41b. The opening/closing switching unit 148 has a switching plate 148a which is operated by driving a motor (not illustrated), and the switching plate 148a is normally located at a position (dotted lines in FIG. 13) which closes the discharge port 41b. The opening/closing switching unit 148 operates the switching plate 148a so that the switching plate 148a is rotated upward to a position (solid line in FIG. 13) where the discharge port 41b is opened by driving of the motor. The opening/closing switching unit 148 is controlled to be opened/closed by the control portion 22. The fine water storage chamber 149 communicates with the air duct 121 so that the fine water discharged from each fine water discharge unit 140 can be temporarily stored. For example, the air duct 121 is formed of a bellows-shaped duct having flexibility so that a position of a discharge port 121a at a tip of the air duct 121 can be adjusted up and down, right and left, and forward and rearward. The air duct 121 discharges the fine water, which is discharged from the fine water discharge unit 140 and is temporarily stored in the fine water storage chamber 149, toward the treatment target. Similarly to the embodiment, the plurality of fine water discharge units 140 repeat the cycle of the cooling, the moisture absorption, the heating, and the moisture release, and is controlled by the unidirectional rotation control (refer to dotted lines in FIG. 7B) for stopping the fan 45 at the time of the heating.

FIG. 14 is an explanatory diagram illustrating a state in which the fine water discharge device 10B is operated in the sequential moisture release mode. As illustrated in FIG. 14, the fine water discharge units 140(1) to 140(4) are controlled so as to be operated while being shifted without synchronizing the cycles of the cooling, the moisture absorption, the heating, and the moisture release. The opening/closing switching units 148 of the fine water discharge units 140(1) to 140(4) are controlled so that the switching plate 148a opens the discharge port 41b at the time of the moisture release, and the switching plate 148a closes the discharge port 41b at the time of the cooling, the moisture absorption, and the heating. Therefore, at the time of the cooling or the moisture absorption, the air blown by the driving of the fan 45 is not rebounded by the switching plate 148a and does not flow into the fine water storage chamber 149, and the fine water is discharged to (flows into) the fine water storage chamber 149 at the time of moisture release. Each of the fine water discharge units 140(1) to 140(4) can discharge (blow) the fine water in the fine water storage chamber 149 from the air duct 121 to the treatment target without interruption while always discharging the fine water from any of the units to the fine water storage chamber 149. Therefore, it is possible to stably supply the fine water to the treatment target while suppressing uneven discharge of fine water. In this modification example, the sequential moisture release mode and the simultaneous moisture release mode can be selected, and the finishing cold air control for simultaneously blowing the cold air from the fine water discharge units 140(1) to 140(4) may be performed before the operation is stopped.

In the modification example, in the opening/closing switching unit 148, the discharge port 41b is opened or closed by the switching plate 148a which is operated so as to rotate upward. However, the present disclosure is not limited to this, and the discharge port 41b may be opened and closed by a shutter which is operated to slide horizontally. The plurality of fine water discharge units 140 may be disposed at equal intervals on the same circumference, and a disk-shaped shutter capable of switching the opening and closing of each discharge port 41b may be disposed. The shutter may have at least one opening formed on the same circumference, and may be configured to be rotatable about a central axis so that the opening sequentially moves to a position corresponding to each discharge port 41b to open the discharge port 41b.

In the embodiment and the modification example, a configuration may be adopted, in which the disk-shaped shutter is provided between one fan 45 and the plurality of fine water generation cartridges 42 and the air from one fan 45 is switchable so as to selectively flow to any one of the fine water generation cartridges 42. That is, in each of the fine water discharge units 40 and 140, one fan 45 and one fine water generation cartridge 42 are configured as one set. However, the plurality of fine water generation cartridges 42, one fan 45, and a switching unit such as a shutter for switching an air blowing destination of the fan 45 may be configured as one set. One set of units may be provided or a plurality of sets of units may be provided.

A correspondence between main elements of the embodiment and main elements of the disclosure described in the section of "SUMMARY" will be described. In the embodiment, the fan 45 corresponds to a "blowing unit", the conductive polymer film 44b corresponds to a "conductive polymer film", the eight fine water generation cartridges 42 correspond a plurality of "fine water generating units", the power supply unit 24 (the power supply circuit 25 and the change-over switch 26) corresponds to an "electrifying portion", the control portion 22 corresponds to a "control portion", and the fine water discharge device 10 corresponds to a "fine water discharge device of a human body". The operation unit 28 corresponds to a "receiving unit". The device main body 20 corresponds to a "device main body", the movable arm 21 corresponds to an "arm", and the discharge head 30 corresponds to a "head".

The correspondence between the main elements of the embodiment and the main elements of the disclosure described in the section of SUMMARY is an example for the embodiment specifically to describe a best mode for carrying out the disclosure described in the section of SUMMARY. Accordingly, the embodiment does not limit the elements of the disclosure described in the section of SUMMARY. That is, an interpretation of the disclosure described in the section of SUMMARY should be interpreted based on the description of the section, and the embodiment is only a specific example of the disclosure described in the section of SUMMARY.

A fine water discharge device of human body according to an aspect of this disclosure discharges fine water to the human body, and the device includes: a plurality of fine water generating units which are brought into a moisture absorption state in which moisture in air is absorbed in a conductive polymer film due to a decrease in temperature and a moisture release state in which the absorbed moisture is released from the conductive polymer film as fine water due to an increase in temperature and are disposed in parallel; a blowing unit which blows air so that air flows through the fine water generating units; an electrifying portion which individually electrifies the plurality of fine water generating units so that a temperature of each fine water generating unit is changed depending on presence or absence of electrification; and a control portion which controls the electrifying portion and the blowing unit so that the plurality of fine water generating units are individually switched between the moisture absorption state and the moisture release state to discharge the fine water by blowing air.

The fine water discharge device of human body according to the aspect of this disclosure includes the plurality of fine water generating unit which are disposed in parallel and the electrifying portion which individually electrifies the plurality of fine water generating units so that the temperature of each fine water generating unit is changed depending on the presence or absence of the electrification, and it is possible to control the electrifying portion and the blowing unit so that the plurality of fine water generating units are individually switched between the moisture absorption state and the moisture release state to discharge the fine water by blowing air. Accordingly, the plurality of fine water generating units can be switched to the moisture release state at any timing irrespective of states of the other fine water generating units and restriction in the operation can be suppressed. Therefore, an operation suitable for a treatment target (discharge target) of the human body such as a face or hair can be performed. The fine water generating unit is configured to release the moisture as uncharged fine water having a particle size of 50 nanometers or less from the conductive polymer film. Accordingly, when the fine water is discharged to the treatment target, the fine water can easily penetrate into a skin, hair, or the like, and a moisturizing effect can be enhanced. When a medicine is applied to the skin or hair, an effect of penetrating the medicine into the skin or hair can be enhanced.

In the fine water discharge device for human body according to the aspect of this disclosure, the blowing unit may include a plurality of fans which are disposed to correspond to the plurality of fine water generating units. According to the configuration, it is possible to easily realize a configuration which can individually blow air to the plurality of fine water generating units. A discharge unit in which one fine water generating unit and one fan are unitized may be configured and a plurality of the discharge units may be disposed in parallel.

In the fine water discharge device of a human body according to the aspect of this disclosure, the blowing unit individually may blow air to the plurality of fine water generating units, and the control portion may control the electrifying portion and the blowing unit in a predetermined moisture release mode in which the plurality of fine water generating units are brought into the moisture release state in a predetermined order and discharge the fine water by blowing air. According to this configuration, the fine water can be easily discharged continuously, and thus, the fine water can be stably supplied to the treatment target.

In the fine water discharge device of human body according to the aspect of this disclosure, the device may further include a receiving unit which receives a selection of one of a plurality of the moisture release modes, and the control portion may control the electrifying portion and the blowing unit in a moisture release mode selected from the plurality of moisture release modes including the predetermined moisture release mode and a moisture release mode in which the plurality of fine water generating units are simultaneously brought into the moisture release state and discharge the fine water by blowing air. In the moisture release mode in which the plurality of fine water generating units are simultaneously brought into the moisture release state, a state where a large amount of fine water exists around the treatment target can be generated. Accordingly, the fine water can be sufficiently supplied to the treatment target. One moisture release mode can be selected from the plurality of moisture release modes in accordance with the treatment target. Accordingly, an operation more suitable for the treatment target can be performed. In each of the moisture release modes, the blowing unit may be controlled to blow air in a predetermined direction in which the fine water is discharged in the moisture release state and the blowing unit may be controlled to blow air in a direction opposite to the predetermined direction in the moisture absorption state, or the air blowing unit may be controlled so as to blow air in a predetermined direction in both the moisture absorption state and the moisture release state.

In the fine water discharge device of a human body according to the aspect of this disclosure, the control portion may control the electrifying portion and the blowing unit to simultaneously blow air in a state where electrification to the plurality of fine water generating units is stopped, before an operation in the moisture release mode ends. According to this configuration, air having a relatively low-temperature is blown toward the treatment target before the operation ends. Accordingly, an effect of tightening a skin of the human body or the like can be exhibited, and the end of the operation can be notified. The temperature of the conductive polymer film can decrease to realize the moisture absorption state. Accordingly, preparation for the next operation can be performed.

The fine water discharge device of human body according to the aspect of this disclosure may further include an arm which is turnably attached to a device main body and has a tip to which a head is attached, in which the plurality of fine water generating units are disposed in parallel in the head so that each of the fine water generating units discharges the fine water from the head. According to this configuration, the fine water can be discharged to the treatment target in a state where the treatment target and each of the fine water generating units are close to each other. Therefore, the fine water can be effectively supplied to the treatment target.

In the fine water discharge device of a human body according to the aspect of this disclosure, the plurality of fine water generating units may be symmetrically disposed in pair with respect to a center of the head, and the control portion may control the electrifying portion and the blowing unit so that each pair of the fine water generating units is switched between the moisture absorption state and the moisture release state at the same timing to discharge the fine water by blowing air. According to this configuration, the fine water can be discharged to be dispersed around the treatment target. Therefore, the fine water can be evenly supplied to the treatment target.

In the fine water discharge device of a human body according to the aspect of this disclosure, the conductive polymer film may be formed of a conductive polymer compound such as a thiophene-based conductive polymer. According to this configuration, it is possible to absorb moisture sufficient to discharge the fine water.

In the fine water discharge device of a human body according to the aspect of this disclosure, the control portion may perform a bidirectional rotation control for rotating the blowing unit in a forward direction and a reverse direction. In addition, in the bidirectional rotation control, the blowing unit may be rotated in the reverse direction in a case where electrification to the electrifying portion is stopped and the blowing unit may be rotated in the forward direction in a case where the electrifying portion is electrified. According to this configuration, although air is blown toward the treatment target at the time of the moisture release, the air cannot be blown toward the treatment target at the time of the cooling or moisture absorption.

Hereinbefore, the best mode for carrying out the present disclosure is described with reference to the embodiments. However, the present disclosure is not limited to the embodiments, and it is needless to say that various modifications may be made within a scope which does not depart from the spirit of the present disclosure.

The present disclosure is applicable to a manufacturing industry of the fine water discharge device of a human body.

The principles, preferred embodiment and mode of operation of the present invention have been described in the foregoing specification. However, the invention which is intended to be protected is not to be construed as limited to the particular embodiments disclosed. Further, the embodiments described herein are to be regarded as illustrative rather than restrictive. Variations and changes may be made by others, and equivalents employed, without departing from the spirit of the present invention. Accordingly, it is expressly intended that all such variations, changes and equivalents which fall within the spirit and scope of the present invention as defined in the claims, be embraced thereby.

What is claimed is:

1. A fine water discharge device of a human body which discharges fine water to the human body, the device comprising:
   a plurality of fine water generating units each including a conductive polymer film, the plurality of fine water generating units are brought into a moisture absorption state in which moisture in the external air is directly absorbed in the conductive polymer film due to a decrease in temperature and a moisture release state in which the absorbed moisture is released from the conductive polymer film as fine water due to an increase in temperature, the plurality of fine water generating units are disposed in parallel;
   a plurality of blowing units that each include a fan, the plurality of blowing units are respectively disposed to correspond to each of the fine water generating unit, the plurality of blowing units are configured to blow air so that air blown from the respective fans flows through a corresponding one of the fine water generating units; wherein the plurality of blowing units each produce a flow path separate from an adjacent flow path produced by the plurality of blowing units;
   an electrifying portion which independently electrifies the plurality of fine water generating units so that a temperature of each fine water generating unit is changed depending on presence or absence of electrification; and
   a control portion includes circuitry which controls the electrifying portion and the fan of each blowing unit of the plurality of blowing units in a predetermined moisture release mode so that the plurality of fine water generating units are independently switched between the moisture absorption state and the moisture release state in a predetermined order so that the discharge device continuously discharges the fine water by blowing air through at least a first one of the plurality of fine water generating units while at least a second one of the plurality of fine water generating units is in the moisture absorption state.

2. The fine water discharge device of a human body according to claim 1, further comprising:
   a receiving unit which receives a selection of one of a plurality of moisture release modes, wherein
   the control portion controls the electrifying portion and the fans in the moisture release mode selected from the plurality of moisture release modes including the predetermined moisture release mode and a moisture release mode in which the plurality of fine water generating units are simultaneously brought into the moisture release state and discharge the fine water by blowing air.

3. The fine water discharge device of a human body according to claim 1, wherein
   the control portion controls the electrifying portion and the fans to simultaneously blow air in a state where electrification to the plurality of fine water generating units is stopped, before an operation in the moisture release mode ends.

4. The fine water discharge device of a human body according to claim 1, further comprising:
   an arm which is turnably attached to a device main body and has a tip to which a head is attached, wherein
   the plurality of fine water generating units are disposed in parallel in the head so that each of the fine water generating units discharges the fine water from the head.

5. The fine water discharge device of a human body according to claim 4, wherein
   the plurality of fine water generating units are symmetrically disposed in pair with respect to a center of the head, and
   the control portion controls the electrifying portion and the fans so that each pair of the fine water generating units is switched between the moisture absorption state and the moisture release state at the same timing to discharge the fine water by blowing air.

6. The fine water discharge device of a human body according to claim 1, wherein
   the conductive polymer film is formed of a conductive polymer compound.

7. The fine water discharge device of a human body according to claim 1, wherein
   the control portion performs a bidirectional rotation control for rotating the plurality of blowing units in a forward direction and a reverse direction.

8. The fine water discharge device of a human body according to claim 7, wherein
   in the bidirectional rotation control, the plurality of blowing units are rotated in the reverse direction in a case where electrification to the electrifying portion is stopped and the plurality of blowing units are rotated in the forward direction in a case where the electrifying portion is electrified.

9. The fine water discharge device of a human body according to claim 1, wherein the circuitry controls the electrifying portion and the fan of each blowing unit of the plurality of blowing units so that the discharge device continuously discharges the fine water by blowing air forward through at least one fine water generating unit of the plurality of fine water generating units while simultaneously blowing air in a reverse direction in at least one adjacent fine water generating units of the plurality of the fine water generating units, such that the at least one fine water generating unit releases moisture while the at least one adjacent fine water generating unit absorbs moisture during the predetermined moisture release mode.

10. A fine water discharge method to a human body which discharges fine water to the human body, the method comprising:
    providing a plurality of fine water generating units each including a conductive polymer film, the plurality of fine water generating units are brought into a moisture absorption state in which moisture in the external air is directly absorbed in the conductive polymer film due to a decrease in temperature and a moisture release state in which the absorbed moisture is released from the conductive polymer film as fine water due to an increase in temperature, the plurality of fine water generating units are disposed in parallel;
    blowing air by a plurality of fans, a fan of the plurality of fans is disposed to respectively correspond to each of the plurality of fine water generating units so that air blown from each fan flows through a corresponding one of the fine water generating units; wherein the plurality of blowing units each produce a flow path separate from an adjacent flow path produced by the plurality of blowing units;

independently electrifying the plurality of fine water generating units so that a temperature of each fine water generating unit is changed depending on presence or absence of electrification; and controlling the blowing and the independently electrifying in a predetermined moisture release mode so that the fine water generating units are independently switched between the moisture absorption state and the moisture release state in a predetermined order so that the discharge method continuously discharges the fine water by blowing air through at least a first one of the plurality of fine water generating units while at least a second one of the plurality of fine water generating units is in the moisture absorption state.

11. The fine water discharge method to a human body according to claim 10, further comprising:

receiving a selection of one of a plurality of the moisture release modes, wherein the controlling controls the electrifying and the blowing in the moisture release mode selected from the plurality of moisture release modes including the predetermined moisture release mode and a moisture release mode in which the plurality of fine water generating units are simultaneously brought into the moisture release state and discharge the fine water by blowing air.

12. The fine water discharge method to a human body according to claim 10, wherein the controlling controls the electrifying and the blowing so as to blow air to the plurality of fine water generating units all at once under absence of the electrifying to the plurality of fine water generating units, before the moisture release mode ends.

13. The fine water discharge method to a human body according to claim 10, further comprising:

turnably attaching a head to a device main body by an arm; and arranging the plurality of fine water generating units in parallel in the head so that each of the fine water generating units discharges the fine water from the head.

14. The fine water discharge method to a human body according to claim 13, wherein the arranging provides pairs of the plurality of fine water generating units symmetrically with respect to a center of the head; and the controlling controls the electrifying and the blowing so that each pair of the fine water generating units is switched between the moisture absorption state and the moisture release state at the same timing to discharge the fine water by blowing air.

15. The fine water discharge method to a human body according to claim 10, further comprising:

forming the conductive polymer film of a conductive polymer compound.

16. The fine water discharge method to a human body according to claim 10, wherein the controlling performs a bidirectional rotation control in the blowing in a forward direction and a reverse direction.

17. The fine water discharge method of a human body according to claim 16, wherein in the bidirectional rotation control, air blows in one direction on the absence of electrification and air blows in the other direction on the presence of electrification.

18. The fine water discharge method of a human body according to claim 10, wherein the controlling controls the blowing and the independently electrifying so that the discharge method continuously discharges to discharge the fine water by blowing air forward through at least one fine water generating unit of the plurality of fine water generating units while simultaneously blowing air in a reverse direction in at least one adjacent fine water generating units of the plurality of the fine water generating units, such that the at least one fine water generating unit releases moisture while the at least one adjacent fine water generating unit absorbs moisture during the predetermined moisture release mode.

* * * * *